US006268341B1

(12) United States Patent
Rosenberg et al.

(10) Patent No.: US 6,268,341 B1
(45) Date of Patent: Jul. 31, 2001

(54) EXPRESSION OF UROKINASE PLASMINOGEN ACTIVATOR INHIBITORS

(75) Inventors: Steven Rosenberg, Oakland; Jennifer R. Stratton-Thomas, San Mateo, both of CA (US)

(73) Assignee: Chiron Corporation, Emeryville, CA (US)

(*) Notice: Subject to any disclaimer, the term of this patent is extended or adjusted under 35 U.S.C. 154(b) by 0 days.

(21) Appl. No.: 09/219,019

(22) Filed: Dec. 23, 1998

Related U.S. Application Data

(62) Division of application No. 08/438,263, filed on May 10, 1995, now abandoned, which is a division of application No. 08/280,288, filed on Jul. 26, 1994, now abandoned, which is a division of application No. 08/070,153, filed on Jun. 1, 1993, now abandoned.

(51) Int. Cl.$^7$ .............................. A61K 38/49; C07K 9/00

(52) U.S. Cl. .............................. 514/12; 514/2; 530/350; 530/324; 536/23.4; 536/23.2; 536/23.1; 435/69.2; 435/69.1

(58) Field of Search .................. 514/12, 2; 530/350, 530/324; 536/23.4, 23.2, 23.1; 435/69.2, 69.1

(56) References Cited

U.S. PATENT DOCUMENTS

| | | | |
|---|---|---|---|
| 4,751,180 | 6/1988 | Cousens et al. | 435/68 |
| 4,791,068 | 12/1988 | Loskutoff et al. | 436/518 |
| 4,835,255 | 5/1989 | Weismann et al. | 530/350 |
| 4,870,008 | * 9/1989 | Brake | 435/70.1 |
| 4,880,734 | 11/1989 | Burke et al. | 435/68 |
| 4,999,194 | 3/1991 | Broeze et al. | 424/94.63 |
| 5,112,755 | 5/1992 | Heyneker et al. | 435/215 |
| 5,219,569 | 6/1993 | Blaber et al. | 424/94.63 |
| 5,340,833 | 8/1994 | Bridges et al. | 514/443 |
| 5,376,547 | 12/1994 | Kaylan et al. | 435/226 |
| 5,389,538 | 2/1995 | Tanabe et al. | 435/215 |
| 5,416,006 | 5/1995 | Blasi et al. | 435/68.1 |
| 5,656,726 | * 8/1997 | Rosenberg et al. | 530/326 |

FOREIGN PATENT DOCUMENTS

| | | |
|---|---|---|
| 64187/94 | 10/1994 | (AU) . |
| 69542/94 | 12/1994 | (AU) . |
| 86/06100 | 10/1986 | (WO) . |
| 92/07083 | 4/1992 | (WO) . |
| 94/22464 | 10/1994 | (WO) . |
| 94/28145 | 12/1994 | (WO) . |

OTHER PUBLICATIONS

Mazar et al, Fibrinolysis, 6, Suppl. 1, 49–55, (1992).*
Estreichert et al, The Jornl. of Biol. Chem., 264(2), 1180–89, (Jan. 15, 1989).*
Rabbani et al, The Journl. of Biol. Chem., 267(20), 1415–56, (Jul. 15, 1992).*
Rabbani et al, BBRC, 173(3), (Dec. 31, 1990), 1058–64.*
Croft, Handbook of Protein Sequence Analysis, 2$^{nd}$ ed. pp. 1–8.66–71.*
Appella, et al., "The Receptor–Binding Sequence Of Urokinase," *J. Biol. Chem.* (Apr. 1987) vol. 262, No. (10):4437–4440.
Brake, "Secretion Of Heterologous Proteins Directed By The Yeast α–Factor Leader," *Yeast Genetic Engineering* (1989) pp.269–280.
Schmitt, et al., "Fluorescent Probes As Tools To Assess The Receptor For The Urokinase–Type," *Seminars Thromb. Hemo.*(Jul. 1991) vol. 17, No. (3):291–302.
Harlow, et al., "Antibodies: A Laboratory Manual," *Cold Spring Harbor Laboratory* (1988) p. 513.
Ito, et al., "Antibodies Against A Nonapeptide of Polyomarvirus Middle T Antigen: Cross–Reaction With A Cellular Protein(s)," *J. Virol.* (Dec. 1983) vol. 48, No. (3):709–720.
Lowman, et al., "Selecting High–Affinity Binding Proteins By Monovalent Phage Display," *Biochemistry* (1991) vol. 30:10832–10838.
Matthews, et al., "Substrate Phage: Selection Of Protease Substrates By Monovalent Phage Display," *Science* (1993) vol. 260:1113–1117.
Nagai, et al., "Molecular Cloning Of cDNA coding For Human Preprourkinase," *Gene* (1985) vol. 36:183–188.
Roldan, et al., "Cloning And Expression Of the Receptor For Human Urokinase Plasminogen Activator, A Central Molecule Of cell Surface, Plasmin Dependent Proteolysis," *EMBO J.* (1990) vol. 9:269–280.
Barr, et al., *Yeast Genetic Engineering* (1989) pp. 269–280.
Frederick, et al., "Glucose Oxidase From Aspergillus Niger," *J. Biological Chemistry*(Mar. 1990) vol. 265, No. 97):3793–3802.
Kingsman and Kingsman, (1990) *Genetic Engineering, Blackwell Scientific Publications*.
Mazar, et al., "Domain Analysis Of Urokinase Plaminogen Activator (u–PA): Preparation And Characterization Of Intact A–Chain Molecules," *Fibrinolysis* 6 (Jan. 1992) (Suppl. 1) pp. 49–55.
Rabbani, et al., "An Amino–Terminal Fragment Of Urokinase . . . ," *Biochem. Biophys. Res. Comm.* (Dec. 1990) vol. 173, No. (3):1058–1064.
Rabbani, et al., "Structural Requirements For The Growth Factor Activity Of The Amino–Terminal Domain Of Urokinase," *J. Biol. Chem.* (Jul. 1992) vol. 267, No. (20):1451–14156.
Corti, et al., "Epitope Mapping Of The Anti–Urokinase Monoclonal Antibody 5B4 By Isolated Domains Of Urokinase," *Thromb. Hemo.* (Nov. 1989) vol. 62, No. (3):934–939.

(List continued on next page.)

Primary Examiner—T. D. Wessendorf
(74) Attorney, Agent, or Firm—David P. Lentini; Robin Teskin; Robert P. Blackburn

(57) ABSTRACT

Unfucosylated huPAR polypeptides that contains huPA$_{1-48}$ (SEQ ID NQ:22) are provided. These polypeptides are useful for treating diseases wherein antagonism of huPAR is therapeutically beneficial.

18 Claims, No Drawings

OTHER PUBLICATIONS

Bowie, et al., "Deciphering The Message In Protein Sequences: Tolerance To Amino Acid Substitutions," *Science* (1990) vol. 247:1307–1310.

Niedbala, et al., "Regulation of Human Squamous Cell Carcinoma Plasma Membrane Associated Urokinase Plasminogen Activator by Epidermal Growth Factor," (Sep. 1990) *Cancer Comm.* vol. 2, No. (9):317–324.

Kobayashi, et al., "Saturation Of Tumor Cell Surface Receptors For Urokinase–Type Plasminogen Activator By Amino–Terminal Fragment And Subsequent Effect On Reconsistuted Basement Membranes Invasion," *Br. J. Cancer* (1993) vol. 67:537–544.

Ballance, et al., "A Hybrid Protein of Urokinase Growth Factor Domain and Plasminogen Activator Inhibitor Type 2 Inhibits Urokinase Activity and Binds to the Urokinase Receptor," (1992) *Eur. J. Biochem* vol. 207, No. (1):177–183.

Stratton–Thomas et al., "Yeast Expression and Phagemid Display of the Human Urokinase Plasminogen Activator Epidermal Growth Factor–Like Domain," Protein Engineering, (1995) vol. 8, No. (5):463–470.

* cited by examiner

SEQUENCE LISTING

```
<160> NUMBER OF SEQ ID NOS: 22

<210> SEQ ID NO 1
<211> LENGTH: 35
<212> TYPE: DNA
<213> ORGANISM: Homo sapiens

<400> SEQUENCE: 1
atgctagatc taatgaactt catcaggtac catcg                                   35

<210> SEQ ID NO 2
<211> LENGTH: 35
<212> TYPE: DNA
<213> ORGANISM: Homo sapiens

<400> SEQUENCE: 2
cgatagatct ttattttgac ttatctattt cacag                                   35

<210> SEQ ID NO 3
<211> LENGTH: 953
<212> TYPE: DNA
<213> ORGANISM: Homo sapiens
<220> FEATURE:
<221> NAME/KEY: CDS
<222> LOCATION: (25)..(903)

<400> SEQUENCE: 3
```

```
ccatggctac agaggaatat aaa atg aat aag gca aaa act tta ctc ttc          51
                         Met Asn Lys Ala Lys Thr Leu Leu Phe
                          1               5 act gcg cta gct ttt ggt tta tct cat caa gct tta gcg gac tac aaa        99
Thr Ala Leu Ala Phe Gly Leu Ser His Gln Ala Leu Ala Asp Tyr Lys
 10              15                  20                  25 gac gat gac gat aag aat tct gac agt gaa tgc ccg ctg agc cac gac       147
Asp Asp Asp Asp Lys Asn Ser Asp Ser Glu Cys Pro Leu Ser His Asp
                 30                  35                  40 ggc tac tgc ctg cac gac ggt gtt tgc atg tac atc gaa gct cta gac       195
Gly Tyr Cys Leu His Asp Gly Val Cys Met Tyr Ile Glu Ala Leu Asp
             45                  50                  55 aag tac gca tgc aac tgc gtt gtt ggg tac atc ggt gag cgc tgc cag       243
Lys Tyr Ala Cys Asn Cys Val Val Gly Tyr Ile Gly Glu Arg Cys Gln
         60                  65                  70 tac cga gat ctt aag tgg tgg gaa ctc cgt ggg ccc ttc gtt tgt gaa       291
Tyr Arg Asp Leu Lys Trp Trp Glu Leu Arg Gly Pro Phe Val Cys Glu
     75                  80                  85 tat caa ggc caa tcg tct gac ctg cct caa cct cct gtc aat gct ggc       339
Tyr Gln Gly Gln Ser Ser Asp Leu Pro Gln Pro Pro Val Asn Ala Gly
 90                  95                 100                 105 ggc ggc tct ggt ggt ggt tct ggt ggc ggc tct gag ggt ggt ggc tct       387
Gly Gly Ser Gly Gly Gly Ser Gly Gly Gly Ser Glu Gly Gly Gly Ser
                110                 115                 120 gag ggt ggc ggt tct gag ggt ggc ggc tct gag gga ggc ggt tcc ggt       435
Glu Gly Gly Gly Ser Glu Gly Gly Gly Ser Glu Gly Gly Gly Ser Gly
            125                 130                 135 ggt ggc tct ggt tcc ggt gat ttt gat tat gaa aag atg gca aac gct       483
Gly Gly Ser Gly Ser Gly Asp Phe Asp Tyr Glu Lys Met Ala Asn Ala
        140                 145                 150 aat aag ggg gct atg acc gaa aat gcc gat gaa aac gcg cta cag tct       531
Asn Lys Gly Ala Met Thr Glu Asn Ala Asp Glu Asn Ala Leu Gln Ser
    155                 160                 165 gac gct aaa ggc aaa ctt gat tct gtc gct act gat tac ggt gct gct       579
Asp Ala Lys Gly Lys Leu Asp Ser Val Ala Thr Asp Tyr Gly Ala Ala
170                 175                 180                 185 atc gat ggt ttc att ggt gac gtt tcc ggc ctt gct aat ggt aat ggt       627
Ile Asp Gly Phe Ile Gly Asp Val Ser Gly Leu Ala Asn Gly Asn Gly
                190                 195                 200 gct act ggt gat ttt gct ggc tct aat tcc caa atg gct caa gtc ggt       675
Ala Thr Gly Asp Phe Ala Gly Ser Asn Ser Gln Met Ala Gln Val Gly
            205                 210                 215 gac ggt gat aat tca cct tta atg aat aat ttc cgt caa tat tta cct       723
Asp Gly Asp Asn Ser Pro Leu Met Asn Asn Phe Arg Gln Tyr Leu Pro
        220                 225                 230 tcc ctc cct caa tcg gtt gaa tgt cgc cct ttt gtc ttt agc gct ggt       771
Ser Leu Pro Gln Ser Val Glu Cys Arg Pro Phe Val Phe Ser Ala Gly
    235                 240                 245 aaa cca tat gaa ttt tct att gat tgt gac aaa ata aac tta ttc cgt       819
Lys Pro Tyr Glu Phe Ser Ile Asp Cys Asp Lys Ile Asn Leu Phe Arg
250                 255                 260                 265 ggt gtc ttt gcg ttt ctt tta tat gtt gcc acc ttt atg tat gta ttt       867
Gly Val Phe Ala Phe Leu Leu Tyr Val Ala Thr Phe Met Tyr Val Phe
                270                 275                 280 tct acg ttt gct aac ata ctg cgt aat aag gag tct taatcatgcg           913
Ser Thr Phe Ala Asn Ile Leu Arg Asn Lys Glu Ser
            285                 290 cgctcactgg ccgtcgtttt acaacgtcgt gactgggaaa                           953
```

-continued

```
<210> SEQ ID NO 4
<211> LENGTH: 293
<212> TYPE: PRT
<213> ORGANISM: Homo sapiens

<400> SEQUENCE: 4

Met Asn Lys Ala Lys Thr Leu Leu Phe Thr Ala Leu Ala Phe Gly Leu
 1               5                  10                  15

Ser His Gln Ala Leu Ala Asp Tyr Lys Asp Asp Asp Lys Asn Ser
            20                  25                  30

Asp Ser Glu Cys Pro Leu Ser His Asp Gly Tyr Cys Leu His Asp Gly
        35                  40                  45

Val Cys Met Tyr Ile Glu Ala Leu Asp Lys Tyr Ala Cys Asn Cys Val
    50                  55                  60

Val Gly Tyr Ile Gly Glu Arg Cys Gln Tyr Arg Asp Leu Lys Trp Trp
65                  70                  75                  80

Glu Leu Arg Gly Pro Phe Val Cys Glu Tyr Gln Gly Gln Ser Ser Asp
                85                  90                  95

Leu Pro Gln Pro Pro Val Asn Ala Gly Gly Ser Gly Gly Ser
            100                 105                 110

Gly Gly Gly Ser Glu Gly Gly Ser Glu Gly Gly Ser Glu Gly
        115                 120                 125

Gly Gly Ser Glu Gly Gly Ser Gly Gly Ser Gly Ser Gly Asp
    130                 135                 140

Phe Asp Tyr Glu Lys Met Ala Asn Ala Asn Lys Gly Ala Met Thr Glu
145                 150                 155                 160

Asn Ala Asp Glu Asn Ala Leu Gln Ser Asp Ala Lys Gly Lys Leu Asp
                165                 170                 175

Ser Val Ala Thr Asp Tyr Gly Ala Ala Ile Asp Gly Phe Ile Gly Asp
            180                 185                 190

Val Ser Gly Leu Ala Asn Gly Asn Gly Ala Thr Gly Asp Phe Ala Gly
        195                 200                 205

Ser Asn Ser Gln Met Ala Gln Val Gly Asp Gly Asp Asn Ser Pro Leu
    210                 215                 220

Met Asn Asn Phe Arg Gln Tyr Leu Pro Ser Leu Pro Gln Ser Val Glu
225                 230                 235                 240

Cys Arg Pro Phe Val Phe Ser Ala Gly Lys Pro Tyr Glu Phe Ser Ile
                245                 250                 255

Asp Cys Asp Lys Ile Asn Leu Phe Arg Gly Val Phe Ala Phe Leu Leu
            260                 265                 270

Tyr Val Ala Thr Phe Met Tyr Val Phe Ser Thr Phe Ala Asn Ile Leu
        275                 280                 285

Arg Asn Lys Glu Ser
    290

<210> SEQ ID NO 5
<211> LENGTH: 953
<212> TYPE: DNA
<213> ORGANISM: Homo sapiens
<220> FEATURE:
<221> NAME/KEY: CDS
<222> LOCATION: (25)..(903)

<400> SEQUENCE: 5
ccatggctac agaggaatat taaa atg aat aag gca aaa act tta ctc ttc      51
                          Met Asn Lys Ala Lys Thr Leu Leu Phe
                           1               5
```

| | | | | | | | | | | | | | | |
|---|---|---|---|---|---|---|---|---|---|---|---|---|---|---|
| act | gcg | cta | gct | ttt | ggt | tta | tct | cat | caa | gct | tta | gcg | gac | tac aaa | 99 |
| Thr | Ala | Leu | Ala | Phe | Gly | Leu | Ser | His | Gln | Ala | Leu | Ala | Asp | Tyr Lys | |
| 10 | | | | | 15 | | | | 20 | | | | | 25 | |

```
act gcg cta gct ttt ggt tta tct cat caa gct tta gcg gac tac aaa       99
Thr Ala Leu Ala Phe Gly Leu Ser His Gln Ala Leu Ala Asp Tyr Lys
 10              15                  20                  25 gac gat gac gat aag aat tct gac agt gaa tgc ccg ctg agc cac gac       147
Asp Asp Asp Asp Lys Asn Ser Asp Ser Glu Cys Pro Leu Ser His Asp
             30                  35                  40 ggc tac tgc ctg cac gac ggt gtt tgc atg tac atc gaa gct cta gac       195
Gly Tyr Cys Leu His Asp Gly Val Cys Met Tyr Ile Glu Ala Leu Asp
         45                  50                  55 aag tac gca tgc aac tgc gtt gtt ggg tac atc ggt gag cgc tgc cag       243
Lys Tyr Ala Cys Asn Cys Val Val Gly Tyr Ile Gly Glu Arg Cys Gln
     60                  65                  70 tac cga gat ctt aag tgg tgg gaa ctc cgt ggg ccc ttc gtt tgt gaa       291
Tyr Arg Asp Leu Lys Trp Trp Glu Leu Arg Gly Pro Phe Val Cys Glu
 75                  80                  85 tat caa ggc caa tcg tct gac ctg cct caa cct cct gtc aat gct ggc       339
Tyr Gln Gly Gln Ser Ser Asp Leu Pro Gln Pro Pro Val Asn Ala Gly
 90                  95                 100                 105 ggc ggc tct ggt ggt ggt tct ggt ggc ggc tct gag ggt ggt ggc tct       387
Gly Gly Ser Gly Gly Gly Ser Gly Gly Gly Ser Glu Gly Gly Gly Ser
                110                 115                 120 gag ggt ggc ggt tct gag ggt ggc ggc tct gag gga ggc ggt tcc ggt       435
Glu Gly Gly Gly Ser Glu Gly Gly Gly Ser Glu Gly Gly Gly Ser Gly
            125                 130                 135 ggt ggc tct ggt tcc ggt gat ttt gat tat gaa aag atg gca aac gct       483
Gly Gly Ser Gly Ser Gly Asp Phe Asp Tyr Glu Lys Met Ala Asn Ala
        140                 145                 150 aat aag ggg gct atg acc gaa aat gcc gat gaa aac gcg cta cag tct       531
Asn Lys Gly Ala Met Thr Glu Asn Ala Asp Glu Asn Ala Leu Gln Ser
    155                 160                 165 gac gct aaa ggc aaa ctt gat tct gtc gct act gat tac ggt gct gct       579
Asp Ala Lys Gly Lys Leu Asp Ser Val Ala Thr Asp Tyr Gly Ala Ala
170                 175                 180                 185 atc gat ggt ttc att ggt gac gtt tcc ggc ctt gct aat ggt aat ggt       627
Ile Asp Gly Phe Ile Gly Asp Val Ser Gly Leu Ala Asn Gly Asn Gly
                190                 195                 200 gct act ggt gat ttt gct ggc tct aat tcc caa atg gct caa gtc ggt       675
Ala Thr Gly Asp Phe Ala Gly Ser Asn Ser Gln Met Ala Gln Val Gly
            205                 210                 215 gac ggt gat aat tca cct tta atg aat aat ttc cgt caa tat tta cct       723
Asp Gly Asp Asn Ser Pro Leu Met Asn Asn Phe Arg Gln Tyr Leu Pro
        220                 225                 230 tcc ctc cct caa tcg gtt gaa tgt cgc cct ttt gtc ttt agc gct ggt       771
Ser Leu Pro Gln Ser Val Glu Cys Arg Pro Phe Val Phe Ser Ala Gly
    235                 240                 245 aaa cca tat gaa ttt tct att gat tgt gac aaa ata aac tta ttc cgt       819
Lys Pro Tyr Glu Phe Ser Ile Asp Cys Asp Lys Ile Asn Leu Phe Arg
250                 255                 260                 265 ggt gtc ttt gcg ttt ctt tta tat gtt gcc acc ttt atg tat gta ttt       867
Gly Val Phe Ala Phe Leu Leu Tyr Val Ala Thr Phe Met Tyr Val Phe
                270                 275                 280 tct acg ttt gct aac ata ctg cgt aat aag gag tct taatcatgcg           913
Ser Thr Phe Ala Asn Ile Leu Arg Asn Lys Glu Ser
            285                 290 cgctcactgg ccgtcgtttt acaacgtcgt gactgggaaa                          953

<210> SEQ ID NO 6
<211> LENGTH: 293
<212> TYPE: PRT
```

<213> ORGANISM: Homo sapiens

<400> SEQUENCE: 6

```
Met Asn Lys Ala Lys Thr Leu Leu Phe Thr Ala Leu Ala Phe Gly Leu
 1               5                  10                  15

Ser His Gln Ala Leu Ala Asp Tyr Lys Asp Asp Asp Lys Asn Ser
                20                  25                  30

Asp Ser Glu Cys Pro Leu Ser His Asp Gly Tyr Cys Leu His Asp Gly
                35                  40                  45

Val Cys Met Tyr Ile Glu Ala Leu Asp Lys Tyr Ala Cys Asn Cys Val
 50                  55                  60

Val Gly Tyr Ile Gly Glu Arg Cys Gln Tyr Arg Asp Leu Lys Trp Trp
 65                  70                  75                  80

Glu Leu Arg Gly Pro Phe Val Cys Glu Tyr Gln Gly Gln Ser Ser Asp
                85                  90                  95

Leu Pro Gln Pro Pro Val Asn Ala Gly Gly Ser Gly Gly Gly Gly Ser
                100                 105                 110

Gly Gly Gly Ser Glu Gly Gly Ser Glu Gly Gly Ser Glu Gly
            115                 120                 125

Gly Gly Ser Glu Gly Gly Ser Gly Gly Ser Gly Ser Gly Asp
        130                 135                 140

Phe Asp Tyr Glu Lys Met Ala Asn Ala Asn Lys Gly Ala Met Thr Glu
145                 150                 155                 160

Asn Ala Asp Glu Asn Ala Leu Gln Ser Asp Ala Lys Gly Lys Leu Asp
                165                 170                 175

Ser Val Ala Thr Asp Tyr Gly Ala Ala Ile Asp Gly Phe Ile Gly Asp
                180                 185                 190

Val Ser Gly Leu Ala Asn Gly Asn Gly Ala Thr Gly Asp Phe Ala Gly
                195                 200                 205

Ser Asn Ser Gln Met Ala Gln Val Gly Asp Gly Asp Asn Ser Pro Leu
        210                 215                 220

Met Asn Asn Phe Arg Gln Tyr Leu Pro Ser Leu Pro Gln Ser Val Glu
225                 230                 235                 240

Cys Arg Pro Phe Val Phe Ser Ala Gly Lys Pro Tyr Glu Phe Ser Ile
                245                 250                 255

Asp Cys Asp Lys Ile Asn Leu Phe Arg Gly Val Phe Ala Phe Leu Leu
                260                 265                 270

Tyr Val Ala Thr Phe Met Tyr Val Phe Ser Thr Phe Ala Asn Ile Leu
                275                 280                 285

Arg Asn Lys Glu Ser
        290
```

<210> SEQ ID NO 7
<211> LENGTH: 60
<212> TYPE: DNA
<213> ORGANISM: Homo sapiens

<400> SEQUENCE: 7
ctcatcaagc tttagcggac tacaaagacg atgacgataa gagcaatgaa cttcatcaag     60

<210> SEQ ID NO 8
<211> LENGTH: 54
<212> TYPE: DNA
<213> ORGANISM: Homo sapiens

<400> SEQUENCE: 8

-continued ctcatcaagc tttagccgaa tacatgccaa tggaaagcaa tgaacttcat caag      54

<210> SEQ ID NO 9
<211> LENGTH: 34
<212> TYPE: DNA
<213> ORGANISM: Homo sapiens

<400> SEQUENCE: 9
caccggaacc ggatccaccc tattttgact tatc                            34

<210> SEQ ID NO 10
<211> LENGTH: 52
<212> TYPE: DNA
<213> ORGANISM: Homo sapiens

<400> SEQUENCE: 10
gaaatagata agtcaaaata gggtggatcc ggttccggtg attttgatta tg        52

<210> SEQ ID NO 11
<211> LENGTH: 22
<212> TYPE: DNA
<213> ORGANISM: Homo sapiens

<400> SEQUENCE: 11
gaaaccatcg atagcagcac cg                                         22

<210> SEQ ID NO 12
<211> LENGTH: 779
<212> TYPE: DNA
<213> ORGANISM: Homo sapiens
<220> FEATURE:
<221> NAME/KEY: CDS
<222> LOCATION: (25)..(729)
<221> NAME/KEY: variation
<222> LOCATION: (259)..(261)
<223> OTHER INFORMATION: amino acid inserted by suppressor strain

<400> SEQUENCE: 12

```
ccatggctac agaggaatat taaa atg aat aag gca aaa act tta ctc ttc        51
                          Met Asn Lys Ala Lys Thr Leu Leu Phe
                           1               5 act gcg cta gct ttt ggt tta tct cat caa gct tta gcc gac tac aaa      99
Thr Ala Leu Ala Phe Gly Leu Ser His Gln Ala Leu Ala Asp Tyr Lys
 10                  15                  20                  25 gac gat gac gat aag agc aat gaa ctt cat caa gtt cca tcg aac tgt     147
Asp Asp Asp Asp Lys Ser Asn Glu Leu His Gln Val Pro Ser Asn Cys
                 30                  35                  40 gac tgt cta aat gga gga aca tgt gtg tcc aac aag tac ttc tcc aac     195
Asp Cys Leu Asn Gly Gly Thr Cys Val Ser Asn Lys Tyr Phe Ser Asn
             45                  50                  55 att cac tgg tgc aac tgc cca aag aaa ttc gga ggg cag cac tgt gaa     243
Ile His Trp Cys Asn Cys Pro Lys Lys Phe Gly Gly Gln His Cys Glu
         60                  65                  70 ata gat aag tca aaa tag ggt gga tcc ggt tcc ggt gat ttt gat tat     291
Ile Asp Lys Ser Lys Gln Gly Gly Ser Gly Ser Gly Asp Phe Asp Tyr
     75                  80                  85 gaa aag atg gca aac gct aat aag ggg gct atg acc gaa aat gcc gat     339
Glu Lys Met Ala Asn Ala Asn Lys Gly Ala Met Thr Glu Asn Ala Asp
 90                  95                 100                 105 gaa aac gcg cta cag tct gac gct aaa ggc aaa ctt gat tct gtc gct     387
Glu Asn Ala Leu Gln Ser Asp Ala Lys Gly Lys Leu Asp Ser Val Ala
                110                 115                 120 act gat tac ggt gct gct atc gat ggt ttc att ggt gac gtt tcc ggc     435
```

-continued

```
ctt gct aat ggt aat ggt gct act ggt gat ttt gct ggc tct aat tcc     483
Leu Ala Asn Gly Asn Gly Ala Thr Gly Asp Phe Ala Gly Ser Asn Ser
        140                 145                 150 caa atg gct caa gtc ggt gac ggt gat aat tca cct tta atg aat aat     531
Gln Met Ala Gln Val Gly Asp Gly Asp Asn Ser Pro Leu Met Asn Asn
    155                 160                 165 ttc cgt caa tat tta cct tcc ctc cct caa tcg gtt gaa tgt cgc cct     579
Phe Arg Gln Tyr Leu Pro Ser Leu Pro Gln Ser Val Glu Cys Arg Pro
170                 175                 180                 185 ttt gtc ttt agc gct ggt aaa cca tat gaa ttt tct att gat tgt gac     627
Phe Val Phe Ser Ala Gly Lys Pro Tyr Glu Phe Ser Ile Asp Cys Asp
                190                 195                 200 aaa ata aac tta ttc cgt ggt gtc ttt gcg ttt ctt tta tat gtt gcc     675
Lys Ile Asn Leu Phe Arg Gly Val Phe Ala Phe Leu Leu Tyr Val Ala
            205                 210                 215 acc ttt atg tat gta ttt tct acg ttt gct aac ata ctg cgt aat aag     723
Thr Phe Met Tyr Val Phe Ser Thr Phe Ala Asn Ile Leu Arg Asn Lys
        220                 225                 230 gag tct taatcatgcg cgctcactgg ccgtcgtttt acaacgtcgt gactgggaaa     779
Glu Ser
    235
```

<210> SEQ ID NO 13
<211> LENGTH: 235
<212> TYPE: PRT
<213> ORGANISM: Homo sapiens

<400> SEQUENCE: 13

```
Met Asn Lys Ala Lys Thr Leu Leu Phe Thr Ala Leu Ala Phe Gly Leu
  1               5                  10                  15

Ser His Gln Ala Leu Ala Asp Tyr Lys Asp Asp Asp Lys Ser Asn
             20                  25                  30

Glu Leu His Gln Val Pro Ser Asn Cys Asp Cys Leu Asn Gly Gly Thr
         35                  40                  45

Cys Val Ser Asn Lys Tyr Phe Ser Asn Ile His Trp Cys Asn Cys Pro
     50                  55                  60

Lys Lys Phe Gly Gly Gln His Cys Glu Ile Asp Lys Ser Lys Gln Gly
 65                  70                  75                  80

Gly Ser Gly Ser Gly Asp Phe Asp Tyr Glu Lys Met Ala Asn Ala Asn
                 85                  90                  95

Lys Gly Ala Met Thr Glu Asn Ala Asp Glu Asn Ala Leu Gln Ser Asp
            100                 105                 110

Ala Lys Gly Lys Leu Asp Ser Val Ala Thr Asp Tyr Gly Ala Ala Ile
        115                 120                 125

Asp Gly Phe Ile Gly Asp Val Ser Gly Leu Ala Asn Gly Asn Gly Ala
    130                 135                 140

Thr Gly Asp Phe Ala Gly Ser Asn Ser Gln Met Ala Gln Val Gly Asp
145                 150                 155                 160

Gly Asp Asn Ser Pro Leu Met Asn Asn Phe Arg Gln Tyr Leu Pro Ser
                165                 170                 175

Leu Pro Gln Ser Val Glu Cys Arg Pro Phe Val Phe Ser Ala Gly Lys
            180                 185                 190

Pro Tyr Glu Phe Ser Ile Asp Cys Asp Lys Ile Asn Leu Phe Arg Gly
        195                 200                 205

Val Phe Ala Phe Leu Leu Tyr Val Ala Thr Phe Met Tyr Val Phe Ser
```

```
              210                 215                 220
Thr Phe Ala Asn Ile Leu Arg Asn Lys Glu Ser
225                 230                 235

<210> SEQ ID NO 14
<211> LENGTH: 773
<212> TYPE: DNA
<213> ORGANISM: Homo sapiens
<220> FEATURE:
<221> NAME/KEY: CDS
<222> LOCATION: (25)..(723)
<221> NAME/KEY: variation
<222> LOCATION: (253)..(255)
<223> OTHER INFORMATION: amino acid inserted by suppressor strain

<400> SEQUENCE: 14
ccatggctac agaggaatat taaa atg aat aag gca aaa act tta ctc ttc          51
                           Met Asn Lys Ala Lys Thr Leu Leu Phe
                             1               5 act gcg cta gct ttt ggt tta tct cat caa gct tta gcc gaa tac atg         99
Thr Ala Leu Ala Phe Gly Leu Ser His Gln Ala Leu Ala Glu Tyr Met
 10              15                  20                  25 cca atg gaa agc aat gaa ctt cat caa gtt cca tcg aac tgt gac tgt        147
Pro Met Glu Ser Asn Glu Leu His Gln Val Pro Ser Asn Cys Asp Cys
                 30                  35                  40 cta aat gga gga aca tgt gtg tcc aac aag tac ttc tcc aac att cac        195
Leu Asn Gly Gly Thr Cys Val Ser Asn Lys Tyr Phe Ser Asn Ile His
             45                  50                  55 tgg tgc aac tgc cca aag aaa ttc gga ggg cag cac tgt gaa ata gat        243
Trp Cys Asn Cys Pro Lys Lys Phe Gly Gly Gln His Cys Glu Ile Asp
         60                  65                  70 aag tca aaa tag ggt gga tcc ggt tcc ggt gat ttt gat tat gaa aag        291
Lys Ser Lys Gln Gly Gly Ser Gly Ser Gly Asp Phe Asp Tyr Glu Lys
     75                  80                  85 atg gca aac gct aat aag ggg gct atg acc gaa aat gcc gat gaa aac        339
Met Ala Asn Ala Asn Lys Gly Ala Met Thr Glu Asn Ala Asp Glu Asn
 90                  95                 100                 105 gcg cta cag tct gac gct aaa ggc aaa ctt gat tct gtc gct act gat        387
Ala Leu Gln Ser Asp Ala Lys Gly Lys Leu Asp Ser Val Ala Thr Asp
                110                 115                 120 tac ggt gct gct atc gat ggt ttc att ggt gac gtt tcc ggc ctt gct        435
Tyr Gly Ala Ala Ile Asp Gly Phe Ile Gly Asp Val Ser Gly Leu Ala
            125                 130                 135 aat ggt aat ggt gct act ggt gat ttt gct ggc tct aat tcc caa atg        483
Asn Gly Asn Gly Ala Thr Gly Asp Phe Ala Gly Ser Asn Ser Gln Met
        140                 145                 150 gct caa gtc ggt gac ggt gat aat tca cct tta atg aat aat ttc cgt        531
Ala Gln Val Gly Asp Gly Asp Asn Ser Pro Leu Met Asn Asn Phe Arg
155                 160                 165 caa tat tta cct tcc ctc cct caa tcg gtt gaa tgt cgc cct ttt gtc        579
Gln Tyr Leu Pro Ser Leu Pro Gln Ser Val Glu Cys Arg Pro Phe Val
170                 175                 180                 185 ttt agc gct ggt aaa cca tat gaa ttt tct att gat tgt gac aaa ata        627
Phe Ser Ala Gly Lys Pro Tyr Glu Phe Ser Ile Asp Cys Asp Lys Ile
                190                 195                 200 aac tta ttc cgt ggt gtc ttt gcg ttt ctt tta tat gtt gcc acc ttt        675
Asn Leu Phe Arg Gly Val Phe Ala Phe Leu Leu Tyr Val Ala Thr Phe
            205                 210                 215 atg tat gta ttt tct acg ttt gct aac ata ctg cgt aat aag gag tct        723
Met Tyr Val Phe Ser Thr Phe Ala Asn Ile Leu Arg Asn Lys Glu Ser
        220                 225                 230
```

```
taatcatgcg cgctcactgg ccgtcgtttt acaacgtcgt gactgggaaa         773
```

<210> SEQ ID NO 15
<211> LENGTH: 233
<212> TYPE: PRT
<213> ORGANISM: Homo sapiens

<400> SEQUENCE: 15

```
Met Asn Lys Ala Lys Thr Leu Leu Phe Thr Ala Leu Ala Phe Gly Leu
 1               5                  10                  15

Ser His Gln Ala Leu Ala Glu Tyr Met Pro Met Glu Ser Asn Glu Leu
            20                  25                  30

His Gln Val Pro Ser Asn Cys Asp Cys Leu Asn Gly Gly Thr Cys Val
        35                  40                  45

Ser Asn Lys Tyr Phe Ser Asn Ile His Trp Cys Asn Cys Pro Lys Lys
    50                  55                  60

Phe Gly Gly Gln His Cys Glu Ile Asp Lys Ser Lys Gln Gly Gly Ser
65                  70                  75                  80

Gly Ser Gly Asp Phe Asp Tyr Glu Lys Met Ala Asn Ala Asn Lys Gly
                85                  90                  95

Ala Met Thr Glu Asn Ala Asp Glu Asn Ala Leu Gln Ser Asp Ala Lys
            100                 105                 110

Gly Lys Leu Asp Ser Val Ala Thr Asp Tyr Gly Ala Ala Ile Asp Gly
        115                 120                 125

Phe Ile Gly Asp Val Ser Gly Leu Ala Asn Gly Asn Gly Ala Thr Gly
    130                 135                 140

Asp Phe Ala Gly Ser Asn Ser Gln Met Ala Gln Val Gly Asp Gly Asp
145                 150                 155                 160

Asn Ser Pro Leu Met Asn Asn Phe Arg Gln Tyr Leu Pro Ser Leu Pro
                165                 170                 175

Gln Ser Val Glu Cys Arg Pro Phe Val Phe Ser Ala Gly Lys Pro Tyr
            180                 185                 190

Glu Phe Ser Ile Asp Cys Asp Lys Ile Asn Leu Phe Arg Gly Val Phe
        195                 200                 205

Ala Phe Leu Leu Tyr Val Ala Thr Phe Met Tyr Val Phe Ser Thr Phe
    210                 215                 220

Ala Asn Ile Leu Arg Asn Lys Glu Ser
225                 230
```

<210> SEQ ID NO 16
<211> LENGTH: 773
<212> TYPE: DNA
<213> ORGANISM: Homo sapiens
<220> FEATURE:
<221> NAME/KEY: CDS
<222> LOCATION: (25)..(723)
<221> NAME/KEY: variation
<222> LOCATION: (253)..(255)
<223> OTHER INFORMATION: amino acid inserted by suppressor strain

<400> SEQUENCE: 16

```
ccatggctac agaggaatat taaa atg aat aag gca aaa act tta ctc ttc        51
                           Met Asn Lys Ala Lys Thr Leu Leu Phe
                            1               5 act gcg cta gct ttt ggt tta tct cat caa gct tta gcg gaa tac atg      99
Thr Ala Leu Ala Phe Gly Leu Ser His Gln Ala Leu Ala Glu Tyr Met
 10                  15                  20                  25 cca atg gaa agc aat gag ctc cat caa gta cca tcg aac tgt gac tgt    147
Pro Met Glu Ser Asn Glu Leu His Gln Val Pro Ser Asn Cys Asp Cys
```

-continued

```
                        30                  35                  40
cta aat gga ggt acc tgt gtg tcc aac aag tac ttt tcg aac att cac        195
Leu Asn Gly Gly Thr Cys Val Ser Asn Lys Tyr Phe Ser Asn Ile His
                45                  50                  55 tgg tgc aat tgc cca aag aaa ttc gga ggg cag cac tgt gaa atc gat        243
Trp Cys Asn Cys Pro Lys Lys Phe Gly Gly Gln His Cys Glu Ile Asp
            60                  65                  70 aag tca aaa tag ggt gga tcc ggt tcc ggt gat ttt gat tat gaa aag        291
Lys Ser Lys Gln Gly Gly Ser Gly Ser Gly Asp Phe Asp Tyr Glu Lys
        75                  80                  85 atg gca aac gct aat aag ggg gct atg acc gaa aat gcc gat gaa aac        339
Met Ala Asn Ala Asn Lys Gly Ala Met Thr Glu Asn Ala Asp Glu Asn
    90                  95                  100                 105 gcg cta cag tct gac gct aaa ggc aaa ctt gat tct gtc gct act gat        387
Ala Leu Gln Ser Asp Ala Lys Gly Lys Leu Asp Ser Val Ala Thr Asp
                    110                 115                 120 tac ggt gct gct atc gat ggt ttc att ggt gac gtt tcc ggc ctt gct        435
Tyr Gly Ala Ala Ile Asp Gly Phe Ile Gly Asp Val Ser Gly Leu Ala
                125                 130                 135 aat ggt aat ggt gct act ggt gat ttt gct ggc tct aat tcc caa atg        483
Asn Gly Asn Gly Ala Thr Gly Asp Phe Ala Gly Ser Asn Ser Gln Met
            140                 145                 150 gct caa gtc ggt gac ggt gat aat tca cct tta atg aat aat ttc cgt        531
Ala Gln Val Gly Asp Gly Asp Asn Ser Pro Leu Met Asn Asn Phe Arg
        155                 160                 165 caa tat tta cct tcc ctc cct caa tcg gtt gaa tgt cgc cct ttt gtc        579
Gln Tyr Leu Pro Ser Leu Pro Gln Ser Val Glu Cys Arg Pro Phe Val
170                 175                 180                 185 ttt agc gct ggt aaa cca tat gaa ttt tct att gat tgt gac aaa ata        627
Phe Ser Ala Gly Lys Pro Tyr Glu Phe Ser Ile Asp Cys Asp Lys Ile
                    190                 195                 200 aac tta ttc cgt ggt gtc ttt gcg ttt ctt tta tat gtt gcc acc ttt        675
Asn Leu Phe Arg Gly Val Phe Ala Phe Leu Leu Tyr Val Ala Thr Phe
                205                 210                 215 atg tat gta ttt tct acg ttt gct aac ata ctg cgt aat aag gag tct        723
Met Tyr Val Phe Ser Thr Phe Ala Asn Ile Leu Arg Asn Lys Glu Ser
            220                 225                 230 taatcatgcg cgctcactgg ccgtcgtttt acaacgtcgt gactgggaaa                 773
```

<210> SEQ ID NO 17
<211> LENGTH: 233
<212> TYPE: PRT
<213> ORGANISM: Homo sapiens

<400> SEQUENCE: 17

```
Met Asn Lys Ala Lys Thr Leu Leu Phe Thr Ala Leu Ala Phe Gly Leu
 1               5                   10                  15

Ser His Gln Ala Leu Ala Glu Tyr Met Pro Met Glu Ser Asn Glu Leu
            20                  25                  30

His Gln Val Pro Ser Asn Cys Asp Cys Leu Asn Gly Thr Cys Val
        35                  40                  45

Ser Asn Lys Tyr Phe Ser Asn Ile His Trp Cys Asn Cys Pro Lys Lys
    50                  55                  60

Phe Gly Gly Gln His Cys Glu Ile Asp Lys Ser Lys Gln Gly Gly Ser
65                  70                  75                  80

Gly Ser Gly Asp Phe Asp Tyr Glu Lys Met Ala Asn Ala Asn Lys Gly
                85                  90                  95

Ala Met Thr Glu Asn Ala Asp Glu Asn Ala Leu Gln Ser Asp Ala Lys
```

```
                    100                 105                 110
Gly Lys Leu Asp Ser Val Ala Thr Asp Tyr Gly Ala Ala Ile Asp Gly
            115                 120                 125

Phe Ile Gly Asp Val Ser Gly Leu Ala Asn Gly Asn Gly Ala Thr Gly
        130                 135                 140

Asp Phe Ala Gly Ser Asn Ser Gln Met Ala Gln Val Gly Asp Gly Asp
145                 150                 155                 160

Asn Ser Pro Leu Met Asn Asn Phe Arg Gln Tyr Leu Pro Ser Leu Pro
                165                 170                 175

Gln Ser Val Glu Cys Arg Pro Phe Val Phe Ser Ala Gly Lys Pro Tyr
            180                 185                 190

Glu Phe Ser Ile Asp Cys Asp Lys Ile Asn Leu Phe Arg Gly Val Phe
            195                 200                 205

Ala Phe Leu Leu Tyr Val Ala Thr Phe Met Tyr Val Phe Ser Thr Phe
        210                 215                 220

Ala Asn Ile Leu Arg Asn Lys Glu Ser
225                 230
```

<210> SEQ ID NO 18
<211> LENGTH: 39
<212> TYPE: DNA
<213> ORGANISM: Homo sapiens

<400> SEQUENCE: 18
agctttagcg gaatacatgc caatggaaag caatgagct                        39

<210> SEQ ID NO 19
<211> LENGTH: 31
<212> TYPE: DNA
<213> ORGANISM: Homo sapiens

<400> SEQUENCE: 19
cattgctttc cattggcatg tattccgcta a                                31

<210> SEQ ID NO 20
<211> LENGTH: 20
<212> TYPE: DNA
<213> ORGANISM: Homo sapiens

<400> SEQUENCE: 20
cgataagtca aaatagggtg                                             20

<210> SEQ ID NO 21
<211> LENGTH: 22
<212> TYPE: DNA
<213> ORGANISM: Homo sapiens

<400> SEQUENCE: 21
gatccaccct attttgactt at                                          22

<210> SEQ ID NO 22
<211> LENGTH: 48
<212> TYPE: PRT
<213> ORGANISM: Homo sapiens

<400> SEQUENCE: 22

```
Ser Asn Glu Leu His Gln Val Pro Ser Asn Cys Asp Cys Leu Asn Gly
  1               5                  10                  15
```

-continued

```
Gly Thr Cys Val Ser Asn Lys Tyr Phe Ser Asn Ile His Trp Cys Asn
            20                  25                  30

Cys Pro Lys Lys Phe Gly Gly Gln His Cys Glu Ile Asp Lys Ser Lys
            35                  40                  45
```

EXPRESSION OF UROKINASE PLASMINOGEN ACTIVATOR INHIBITORS

This application is a divisional of Ser. No. 08/438,263, filed May 10, 1995, now abandoned which is a divisional of Ser. No. 08/280,288, filed Jul. 26, 1994, now abandoned, which is a continuation of application Ser. No. 08/070,153, filed Jun. 1, 1993, now abandoned.

DESCRIPTION

1. Technical Field

This invention relates to the fields of cellular biology and protein expression. More particularly, the invention relates to peptide ligands of the urokinase plasminogen activator receptors and methods for preparing the same.

2. Background Of The Invention

Urokinase-type plasminogen activator (uPA) is a multi-domain serine protease, having a catalytic NBN chain (amino acids 144411), and an amino-terminal fragment ("ATF", aa 1–143) consisting of a growth factor-like domain (443) and a kringle (aa 47–135). The uPA kringle appears to bind heparin, but not fibrin, lysine, or aminohexanoic acid. The growth factor-like domain bears some similarity to the structure of epidermal growth factor (EGF), and is thus also refered to as an "EGF-like" domain. The single chain pro-uPA is activated by plasmin, cleaving the chain into the two chain active form, which is linked together by a disulfide bond.

uPA binds to its specific cell surface receptor (uPAR). The binding interaction is apparently mediated by the EGF-like domain (S. A. Rabbani et al., *J Biol Chem* (1992) 267:14151–56). Cleavage of pro-uPA into active uPA is accelerated when pro-uPA and plasminogen are receptor-bound. Thus, plasmin activates pro-uPA, which in turn activates more plasmin by cleaving plasminogen. This positive feedback cycle is apparently limited to the receptor-based proteolysis on the cell surface, since a large excess of protease inhibitors is found in plasma, including ce antiplasmin, PAI-1 and PAI-2.

Plasmin can activate or degrade extracellular proteins such as fibrinogen, fibronectin, and zymogens. Plasminogen activators thus can regulate extracellular proteolysis, fibrin clot lysis, tissue remodeling, developmental cell migration, inflammation, and metastasis. Accordingly, there is great interest in developing uPA inhibitors and uPA receptor antagonists. E. Appella et al., *J Biol Chem* (1987) 262:443740 determined that receptor binding activity is localized in the EGF-like domain, and that residues 12–32 appear to be critical for binding. The critical domain alone ($uPA_{12-32}$) bound uPAR with an affinity of 40 nM (about 100 fold less than intact ATF).

S. A. Rabbani et al., supra, disclosed that the EGF-like domain is fucosylated at $Thr_{18}$, and reported that fucosylated EGF-like domain ($uPA_{4-43}$, produced by cleavage from prouPA) was mitogenic for an osteosarcoma cell line, SaOS-2. In contrast, non-fucosylated EGF-like domain bound uPAR with an affinity equal to the fucosylated EGF-like domain, but exhibited no mitogenic activity. Non-fucosylated EGF-like domain competed for binding to uPAR with fucosylated EGF-like domain, and reduced the mitogenic activity observed. Neither EGF-iike domain was mitogenic in U937. fibroblast cells.

Previously, it was suggested that an "epitope libqry" might be made by cloning synthetic DNA that encodes random peptides into filamentous phage vectors (Parnley and Smith, Gene (1988) 73:305). It was proposed that the synthetic DNA be cloned into the coat protein gene III because of the likelihood of the encoded peptide becoming part of pIII without significantly interfering with pIII's function. It is known that the amino terminal half of pIII binds to the F pilus during infection of the phage into *E. coli*. It was suggested that such phage that carry and express random peptides on their cell surface as part of pIII may provide a way of identifying the epitopes recognized by antibodies, particularly using antibody to affect the purification of phage from the library. Devlin, PCT WO91/18980 (incorporated herein by reference) described a method for producing a library consisting of random peptide sequences presented on tilamentous phage. The library can be used for many purposes, including identifying and selecting peptides that have a particular bioactivity. An example of a ligand binding molecule would be a soluble or insoluble cellular receptor (i.e., a membrane bound receptor), but would extend to virtually any molecule, including enzymes, that have the sought after binding activity. Description of a similar library is found in Dower et al., WO91/19818. The present invention provides a method for screening such libraries (and other libraries of peptides) to determine bioactive peptides or compounds. Kang et al., WO92/18619 disclosed a phage library prepared by inserting into the pVIII gene.

However, both the pIII and pVIII proteins are expressed in multiple copies in filamentous bacteriophage. As a result, the phage are selected and amplified based on their avidity for the target, rather than their affinity. To overcome this problem, a method for monovalent (only one test peptide per phage) phage display has been developed (H. B. Lowman et al., *Biochem* (1991) 30:10832–38). To obtain monovalent display, the bacterial host is coinfected with the phage library and a large excess of "helper" phage, which express only wild-type pIII (and/or pVIII) and are inefficiently packaged. By adjusting the ratio of display phage to helper phage, one can adjust the ratio of modified to wild-type display proteins so that most phage have only one modified protein. However, this results in a large amount of phage having only wild-type pIII (or pVIII), which significantly raises the background noise of the screening.

DISCLOSURE OF THE INVENTION

One aspect of the invention is a method for producing non-fucosylated uPA EGF-like domain, particularly $uPA_{1-48}$ (SEQ ID NO: 22).

Another aspect of the invention is non-fucosylated $uPA_{1-48}$, (SEQ ID NO: 22) which is useful for inhibiting the mitogenic activity of uPA in cancer cells.

Another aspect of the invention is a method for treating cancer and metastasis by administering an effective amount of a non-fucosylated uPA EGF-like domain, particularly $uPA_{1-48}$. (SEQ ID NO: 22)

Another aspect of the invention is a method for pre-enriching a monovalent phage display mixture prior to screening for binding to a target, by providing a mixture of monovalent display phage and non-displaying phage, wherein the monovalent display phage display both a candidate peptide and a common peptide, the common peptide is identical for each monovalent display phage, and the candidate peptide is different for different monovalent display phage; and separating all phage displaying the common peptide from phage not displaying a common peptide.

MODES OF CARRYING OUT THE INVENTION

A. Definitions

The term "huPA" refers specifically to human urokinase-type plasminogen activator. The "EGP-like domain" is that portion of the huPA molecule responsible for mediating huPA binding to its receptor (uPAR). The EGF-like domain, sometimes called the growth factor-like domain ("GFD"), is located within the first 48 residues of huPA. The critical residues (essential for binding activity) have been localized to positions 12–32, although a peptide containing only those residues does not exhibit a binding affinity high enough to serve as a useful receptor antagonist.

The term "huPAR antagonist polypeptide" refers to a polypeptide having a sequence identical to the EGF-like domain of huPA (residues 148), or an active portion thereof. An "active portion" is one which lacks up to 10 amino acids, from the N-terminal or C-terminal ends, or a combination thereof, of the huPA$_{48}$ polypeptide, and exhibits a $K_d \leq 5$ nM with huPAR. The term "active analog" refers to a polypeptide differing from the sequence of the EGF-like domain of huPA$_{1-48}$ or an active portion thereof by 1–7 amino acids, but which still exhibits a $K_d \leq 5$ nM with huPAR. The differences are preferably conservative amino acid substitutions, in which an amino acid is replaced with another naturally-occurring amino acid of similar character. For example, the following substitutions are considered "conservative": Gly↔Ala; Val↔Ile↔Leu; Asp↔Glu; Lys↔Arg; Asn↔Gln; and Phe↔Trp↔Tyr. Nonconservative changes are generally substitutions of one of the above amino acids with an amino acid from a different group (e.g., substituting Asn for Glu), or substituting Cys, Met, His, or Pro for any of the above amino acids. The huPAR antagonist polypeptides of the invention should be substantially free of peptides derived from other portions of the huPA protein. For example, a huPAR antagonist composition should contain less than 20 wt % uPA B domain (dry weight, absent excipients), preferably less than 10 wt % uPA-B, more preferably less than 5 wt % uPA-B, most preferably no detectable amount. The huPAR antagonist polypeptides also preferably exclude the kringle region of uPA.

The term "expression vector" refers to an oligonucleotide which encodes the huPAR antagonist polypeptide of the invention and provides the sequences necessary for its expression in the selected host cell. Expression vectors will generally include a transcriptional promoter and terminator, or will provide for incorporation adjacent to an endogenous promoter. Expression vectors will usually be plasmids, further comprising an origin of replication and one or more selectable markers. However, expression vectors may alternatively be viral recombinants designed to infect the host, or integrating vectors designed to integrate at a preferred site within the host's genome. Expression vectors may further comprise an oligonucleotide encoding a signal leader polypeptide. When "operatively connected", the huPAR antagonist is expressed downstream and in frame with the signal leader, which then provides for secretion of the huPAR antagonist polypeptide by the host to the extracellular medium. Presently preferred signal leaders are the *Saccharomyces cerevsiae* α-factor leader (particularly when modified to delete extraneous Glu-Ala sequences), and the ubiquitin leader (for intracellular expression).

The term "transcriptional promoter" refers to an oligonucleotide sequence which provides for regulation of the DNA→mRNA transcription process, typically based on temperature, or the presence or absence of metabolites, inhibitors, or inducers. Trancriptional promoters may be regulated (inducible/repressible) or constitutive. Yeast glycolytic enzyme promoters are capable of driving the transcription and expression of heterologous proteins to high levels, and are particularly preferred. The presently preferred promoter is the hybrid ADH2/GAP promoter described in TekampOlson et al., U.S. Pat. No. 4,876,197 (incorporated herein by reference), comprising the *S. cerevisiae* glyceraldehyde-3-phospbate dehydrogenase promoter in combination with the *S. cerevisiae* alcohol dehydrogenase II upstream activation site.

The term "host" refers to a yeast cell suitable for expressing heterologous polypeptides. There are a variety of suitable genera, such as Saccharomyces, Schizosaccharomnyces, Kluveronzyces, Pichia, Hansenuzla, and the like. Presently preferred are yeast of the Saccharomnyces genus, particularly *Saccharomyces cerevisiae*.

The term "uPA-mediated disorder" refers to a disease state or malady which is caused or exacerbated by a biological activity of uPA. The primary biological activity exhibited is plasminogen activation. Disorders mediated by plasminogen activation include, without limitation, inappropriate angiogenesis (e.g., diabetic retinopathy, corneal angiogenesis, Kaposi's sarcoma, and the like), metastasis and invasion by tumor cells, and chronic inflammation (e.g., rheumatoid arthritis, emphysema, and the like). Fucosylated ATF is also mitogenic for some tumor cells (e.g., SaOS-2 osteosarcoma cells), which sometimes self-activate in an autocrine mechanism. Accordingly, the huPAR antagonist of the invention is effective in inhibiting the proliferation of uPA-activated tumor cells.

The term "effective amount" refers to an amount of huPAR antagonist polypeptide sufficient to exhibit a detectable therapeutic effect. The therapeutic effect may include, for example, without limitation, inhibiting the growth of undesired tissue or malignant cells, inhibiting inappropriate angiogenesis, limiting tissue damage caused by chronic inflammation, and the like. The precise effective amount for a subject will depend upon the subject's size and health, the nature and severity of the condition to be treated, and the like. Thus, it is not possible to specify an exact effective amount in advance. However, the effective amount for a given situation can be determined by routine experimentation based on the information provided herein.

The term "pharmaceutically acceptable" refers to compounds and compositions which may be administered to mammals without undue toxicity. Exemplary pharmaceutically acceptable salts include mineral acid salts such as hydrochlorides, hydrobromides, phosphates, sulfates, and the like; and the salts of organic acids such as acetates, propionates, malonates, benzoates, and the like.

The term "pre-enriching" refers to increasing the concentration of candidate phage in a monovalent phage display mixture by removing phage which do not have a candidate peptide. A "monovalent phage display mixture" is a mixture of phage containing recombinant phage and helper phage in a ratio such that most phage display at most one recombinant surface protein.

The term "common peptide" refers to a distinctive heterologous (not wild-type) peptide sequence which is displayed identically by all recombinant members of a phage (or other host) library. The common peptide is preferably an epitope recognized by a high-affinity antibody, which is not cross-reactive with any epitopes naturally occurring in the wild-type phage. The common peptide permits one to select all recombinant phage (having a common peptide and a random candidate peptide) as a set, and purify them away from non-recombinant (wild-type) phage. The presently preferred common peptide is Glu-Tyr-Met-Pro-Met-Glu.

B. General Method

The present invention relies on the fact that yeast do not fucosylate proteins upon expression, but are able to express properly folded, active uPA and fragments. One may employ other eukaryotic hosts in the practice of the invention as long as the host is incapable of fucosylating proteins, whether naturally or due to manipulation (e.g., genetic mutation or antibiotic treatment). Presently preferred hosts are yeasts, particularly Saccharomyces, Schizosaccharonyces, Kluveronyces, Pichia, Hansenula, and the like, especially *S. cerevisiae*. Stains AB110 and MB2-1 are presently preferred.

The expression vector is constructed according to known methods, and typically comprises a plasmid functional in the selected host. The uPA sequence used may be cloned following the method described in Example 1 below. Variations thereof (i.e., active fragments and active analogs) may be generated by site-specific mutagenesis, imperfect PCR, and other methods known in the art. Stable plasmids generally require an origin of replication (such as the yeast $2\mu$ ori), and one or more selectable markers (such as antibiotic resistance) which can be used to screen for transformants and force retention of the plasmid. The vector should provide a promoter which is functional in the selected host cell, preferably a promoter derived from yeast glycolytic enzyme promoters such as GAPDH, GAL, and ADH2. These promoters are highly efficient, and can be used to drive expression of heterologous proteins up to about 10% of the host cell weight. The presently preferred promoter is a hybrid ADH2IGAP promoter comprising the *S. cerevisiae* glyceraldehyde-3-phosphate dehydrogenase promoter in combination with the *S. cerevisiae* alcohol dehydrogenase II upstream activation site.

The expression vector should ideally provide a signal leader sequence between the promoter and the huPAR antagonist polypeptide sequence. The signal leader sequence provides for translocation of the huPAR antagonist polypeptide through the endoplasmic reticulum and export from the cell into the extracellular medium, where it may be easily harvested. There are a number of signal leader sequences known that are functional in yeast. The yeast α-factor leader is presently preferred (see U.S. Pat. No. 4,751,180, incorporated herein by reference).

Alternatively, the vector may provide for integration into the host genome, as is described by Shuster, PCT WO92/01800, incorporated herein by reference.

Transformations into yeast can be carried out according to the method of A. Hinnen et al., *Proc Natl Acad Sci USA* (1978) 75:1929–33, or H. Ito et al., *J Bacteriol* (1983) 15: 163–68. After DNA is taken up by the host cell, the vector integrates into the yeast genome at one or more sites homologous to its targeting sequence. It is presently preferred to linearize the vector by cleaving it within the targeting sequence using a restriction endonuclease, as this procedure increases the efficiency of integration.

Following successful transformations, the number of integrated sequences may be increased by classical genetic techniques. As the individual cell clones can carry integrated vectors at different locations, a genetic cross between two appropriate strains followed by sporulation and recovery of segregants can result in a new yeast strain having the integrated sequences of both original parent strains. Continued cycles of this method with other integratively transformed strains can be used to further increase the copies of integrated plasmids in a yeast host strain. One may also amplify the integrated sequences by standard techniques, for example by treating the cells with increasing concentrations of copper ions (where a gene for copper resistance has been included in the integrating vector).

Correct ligations for plasmid construction may be confirmed by first transforming *E. coli* strain MM294 obtained from *E. coli* Genetic Stock Center, CGSC #6135, or other suitable host with the ligation mixture. Successful transformants are selected by ampicillin, tetracycline or other antibiotic resistance or using other markers depending on the plasmid construction, as is understood in the art. Plasmids from the transformants are then prepared according to the method of D. B. Clewell et al., *Proc Natl Acad Sci USA* (1969) 62:1159, optionally following chloramphenicol amplification (D. B. Clewell, *J Bacteriol* (1972) 110:667). Isolated DNA is analyzed by restriction mapping and/or sequenced by the dideoxy method of F. Sanger et al., *Proc Natl Acad Sci USA* (1977) 74:5463 as further described by Messing et al., *Nucl Acids Res* (1981) 9:309, or by the method of Maxam and Gilbert, *Meth Enzymol* (1980) 65:499.

huPAR antagonist polypeptides may be assayed for activity by methods known in the art For example, one may assay competition of the antagonist against native uPA for cell surface receptor binding. Competition for the receptor correlates with inhibition of uPA biological activity. One may assay huPAR antagonist polypeptides for anti-mitogenic activity on appropriate tumor cell lines, such as the osteosarcoma cell line SaOS-2 described in the art. Inhibition of mitogenic activity may be determined by comparing the uptake of $^3$H-T in osteosarcoma cells treated with the antagonist against controls. One may also assay huPAR antagonists for anti-invasive activity on appropriate tumor cell lines, such as HOC-1 and HCT116 (W. Schlechte et al., *Cancer Comm* (1990) 2:173–79; H. Kobayashi et al., *Brit J Cancer* (1993) 67:537–44).

huPAR antagonists are administered orally, topically, or by parenteral means, including subcutaneous and intramuscular injection, implantation of sustained release depots, intravenous injection, intranasal administration, and the like. When used to treat tumors, it may be advantageous to apply the huPAR antagonist directly to the site, e.g., during surgery to remove the bulk of the tumor. Accordingly, huPAR antagonist may be administered as a pharmaceutical composition comprising huPAR antagonist in combination with a pharmaceutically acceptable excipient. Such compositions may be aqueous solutions, emulsions, creams, ointments, suspensions, gels, liposomal suspensions, and the like. Suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, CARBOPOL® acrylic acid-based polymers (available commercially from BF Goodrich of Cleveland, Ohio), vegetable oils, and the like. One may additionally include suitable preservatives, stabilizers, anti-oxidants, antimicrobials, and buffering agents, for example, BHA, BHT, citric acid, ascorbic acid, tetracycline, and the like. Cream or ointment bases useful in formulation include lanolin, SILVADENE® (silver sulfadiazine) (Marion), AQUAPHOR® petroleum and mineral oil mixture (available commercially from Beirsdorf, Inc. of Norwalk, Conn.), and the like. Other topical formulations include aerosols, bandages, and other wound dressings. Alternatively, one may incorporate or encapsulate the huPAR antagonist in a suitable polymer matrix or membrane, thus providing a sustained-release delivery device suitable for implantation near the site to be treated locally. Other devices include indwelling catheters and devices such as the ALZET® mintpump (available commercially from Alza Corporation, Mountain View, Calif.). Ophthalmic preparations may be formulated using commercially available vehicles such as (Allergan), steroid-antibiotic combinations such as NEODECADRON® (dexamethasone sodium phosphate and neomycin sulfate combination, available commercially from Merck & Co., Inc., Whitehouse Station, N.J.). and the like, or may employ topical preparations such as that described in U.S. Pat. No. 5,124,155, incorporated herein by reference. Further, one may provide a huPAR antagonist in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in *Remington's Pharmaceutical Sciences* (Mack Pub. Co.).

The amount of huPAR antagonist required to treat any particular disorder will of course vary depending upon the nature and severity of the disorder, the age and condition of the subject, and other factors readily determined by one of ordinary skill in the art. The appropriate dosage may be determined by one of ordinary skill by following the methods set forth below in the examples. As a general guide, about 0.01 mg/Kg to about 50 mg/Kg huPAR antagonist administered i.v. or subcutaneously is effective for inhibiting tissue damage due to chronic inflammation. For treating corneal angiogenesis, huPAR antagonist may be administered locally in a gel or matrix at a concentration of about 0.001 mg/Kg to about 5 mg/Kg.

C. EXAMPLES

The examples presented below are provided as a further guide to the practitioner of ordinary skill in the art, and are not to be construed as limiting the invention in any way.

Example 1

(Cloning and Expression of huPA$_{1-48}$)

DNA encoding residues 1–48 of mature human uPA (huPA) was cloned into a yeast expression vector as a fusion with the yeast alpha-factor leader (αFl), under transcriptional control of a hybrid ADH2-GAP promoter. The αFl is described in Brake, U.S. Pat. No. 4,870,008, incorporated herein by reference. The hybrid ADH2-GAP promoter is described in TekampOlson et al., U.S. Pat. No. 4,876,197, and Tekamp-Olson et al., U.S. Pat. No. 4,880,734, both incorporated herein by reference.

The gene encoding huPA was obtained by PCR using the following sense and nonsense primers:
5'-ATGCTAGATCTAATGAACTTCATCAGGTACCATCG-3' (SEQ ID NO: 1), and
5'-CGATAGATCTTTATTTTGACTTATCTATTTCACAG-3' (SEQ ID NO:2).
Each of the above primers introduces a BglII site at the ends for cloning into the expression vector. Additionally, the sense strand primer introduces a KpnI site 14 nucleotides downstream from the signal peptide cleavage site, and the nonsense strand primer introduces a stop codon after Lys at position 48. The template DNA used was a clone of full length mature huPA in a yeast expression vector, as an alpha-factor fusion (pAB24UK300, consisting of the yeast shuttle vector pAB24 having a cassette inserted at the BamHI site, the cassette containing the ADH2-GAP hybrid promoter, the yeast a-factor leader, the coding sequence for mature human uPA, and the GAP terminator, obtained from P. Valenzuela, Chiron Corporation) derived from a human kidney CDNA library M. A. Truett et al., *DNA* (1985) 4:33349). Polymerase chain reactions were carried out in 100 µL volumes with the following components: 10 mM Tris-HCl, pH 8.3, 50 mM KCl, 1.5 mM MgCl$_2$, 0.2 mM each DATP, dCJP, dGTP, and dew, 1 1M each primer, 9 ng template plasmid, and 2.5 U Taq DNA polymerase. The reaction conditions were 94° C. for 1 min, followed by 37° C. for 2 min, then 72° C. for 3 min, for 30 cycles. Both the PCR fragment and a subcloning vector (CBR, described by Frederik et al., *J Biol Chem* (1990) 265:3793) containing the yeast expression cassette were digested with BglII and then ligated together, after treatment of the pCBR vector with alkaline phosphatase. Once the subclone was obtained (pCBRuPAα13), the expression cassette was isolated via BamHi digestion and ligated into the yeast shuttle vector (pAB24) to yield pAB24α3uPA1-48.

The expression plasmid was transformed into *Saccharomyces cerevisiae* AB110 (MATα leu2-3-112 ura3-52 pep4-3 [cir⁰]) using the lithium acetate method (Ito et al., *J Bacteriol* (1983) 153:163), and selected for uracil prototrophy. The plasmid copy number was then amplified by growth on minimal media without leucine, containing 8% glucose to keep ADH2-GAP promoter-mediated expression repressed. High level expression of secreted huPAIa was obtained with pAB24α13uPA$_{1-48}$ transformants of AB110 grown in leu⁻ medium and inoculating at 1:10 into YEP 4% glucose medium. All yeast cultures were grown at 30° C., 275 rpm, for 96 hours.

Example 2

(Purification of huPA$_{1-48}$)

One liter of yeast supernatant was harvested by centrifuging the cells at 2600×g. Protein was concentrated from the supernatant by adding 70% ammonium sulfate, incubating for 1 hr at 4° C., and separating the protein precipitate by centrifuging at 11,000×g for 1 hr at 4° C. The protein pellets were resuspended in buffer containing 20 mM potassium phosphate, pH 7.0, 50 mM NaCl, and 1 mM EDTA. The suspension was dialyzed against the same buffer, with two changes of 4 L, overuight at 4° C. The entire dialysate was loaded onto a 1.8 L SEPHADEX® G-50 (Sigma, St. Louis, Mo.) column at room temperature. Fractions were collected and monitored with UV at 254 nm, then pooled based on 16% Tris-Tricine SDS-PAGE (Novex) under non-reducing conditions. The peak fractions, containing monomeric huPAI$_4$g, were then loaded onto a 22 mm C18 reverse phase HPLC column (Vydac) and the protein eluted with a 0.6% gradient of acetonitrile containing 1% TFA. The major peak eluting at 33.5 minutes was collected and lyophilized. The purification yield is summarized in Table 1:

TABLE 1

| | Purification of huPA$_{1-48}$ | | |
|---|---|---|---|
| Sample | Total Protein | Total Units[b] | Yield |
| Crude supernatant | ~200 mg[a] | 3.3 × 10⁶ | — |
| Ammonium sulfate | 160 mg | 2.0 × 10⁶ | 60% |
| G50 Column | 103 mg | 1.3 × 10⁶ | 42% |
| HPLC Purified | 8.4 mg | 7.4 × 10⁵ | 22% |

[a]Estimated protein concentration due to interference with BCA assay
[b]Unit = volume of crude sample required to inhibit binding of $^{125}$I-ATF 50% in competition with biotinylated suPAR.

Example 3

(Characterization of huPA$_{1-48}$).

Purified huPA$_{1-48}$ was subjected to amino acid analysis and N-terminal sequencing, yielding the expected composition and sequence. The Edman degradation was performed through residue 20. A stoichiometric amount of threonine was observed at cycle 18, indicating that this residue was not modified by fucosylation, as is found for uPA purified from eukaryotic cells. The absence of post translational modification was later confirmed by electrospray mass spectrometry. The binding activity of the recombinant huPA$_{1-48}$ was determined using a radio-receptor binding assay.

Baculovirus-derived recombinant human urokinase receptor was expressed as a truncated, soluble molecule as described previously for mouse L-cells (Masucci et al., *J Biol Chem* (1991) 266:8655). The purified receptor was biotinylated with NHS-biotin, and immobilized at 1 µg/mL in PBS/0.1% BSA on streptavidin coated 96-well plates. Human uPA ATF (residues 1–135, obtained from M. Shuman, University of California, San Francisco) was iodinated using the Jodogen method (Pierce), and used as tracer. The $^{125}$I-ATF was incubated at 100–500 pM with increasing amounts of huPA$_{1-48}$ in triplicate (100 pM–1 µM) for 2 hours at room temperature in 0.1% BSA/PBS in a total volume of 200 µL. The plates were then washed 3 times with PBSIBSA, and the remaining bound radioactivity determined. The apparent Kd observed for huPA$_{1-48}$ was 0.3 nM, comparable to that reported for ATF and intact uPA.

Example 4

(Construction of huPA$_{1-48}$ Muteins)

In order to efficiently analyze the features of huPA$_{1-48}$, we performed a series of mutagenesis experiments utilizing phage display. Attempts to employ the system described by Scott and Smith, *Science* (1990) 249:38690, were not successful. However, the use of monovalent phage display, using a phagemid and helper phage as described by Lowman et al., *Biochem* (1991) 3:10832–38, did result in functional display of the protein domain. Finally, we employed an affinity epitope "tag" to reduce the fraction of phage bearing only wild-type pIII protein, reducing the background in panning experiments.
A.) Construction of Phagemids:

The starting materials were a phagemid construct (pGMEGF) comprising a human epidermal growth factor (hEGF) gene linked to the lac promoter, using pBluescript (Stratagene) as the backbone. The polylinker region of the vector contained within a PvuII fragment was replaced by a cassette comprising a leader sequence from the photobacterial superoxide dismutase fused to a synthetic gene for hEGF, in turn fused to residues 198–406 of the M13 pIII gene. The sequence of the insert is shown in SEQ ID NO:3. A synthetic gene encoding human urokinase residues 148 was obtained from J. Stratton-Thomas, Chiron Corporation.

Fusion proteins were generated using PCR. A first set of primers EUPCR1 and EUKGPCR1 were used with primer ELKPCR2 to add epitope tags to huPA$_{1-48}$, at the N-terminus, and to add an amber codon (TAG) and a BamiHI site within residues 249–254 of the pIII protein at the C-terminus.
EUKMPCR1: CTrCATCAAGCTTTAGCGGACTACAAA-GACGATGACGATAAGAGCAATCAACTTCATCAAG (SEQ ID NO:7);
EUKGPCR1: CTCATCAAGCTTTAGCCGAATACATGC-CAATGGAAAGCAATGAACTTCATCAAG (SEQ ID NO:8);
EUKPCR2: CACCGGAACCGGATCCAC-CCTATTTTGACTTATC (SEQ ID NO:9).
The PCR reactions yielded primary products of the expected sizes, 204 and 197 bp.

A second set of primers, SRO1 and EUKCPCR1, were used with the EGF-containing phagemid construct as template. These primers added a BamHI site at pIII residues 250–251 and amplified a fragment ending at the unique Cla1 site at residues 297–299 of pIII.
SRO1: GAAATAGATAAGTCAAAATAGGGTG-GATCCGGTrCCGGTGATTTTGATTATG (SEQ ID NO:8); and
EUKCPCRI: GAAACCATCGATAGCAGCACCG (SEQ ID NO:9).

This PCR reaction yielded a primary product of approximately 180 bp. The PCR reaction products were separated from unreacted primers by size exclusion chromatography (Chromaspin-100, Clontech), digested with restriction enzymes Hd3 and amHI (set 1) or BamHI and Cla1 (set 2), and isolated from a 2.5% agarose gel, using the Mermaid procedure (Bio-101) Each of the set 1 fragments were ligated with the C-terminal reaction 2 fragment, the ligations digested with Hd3 and Cla1, and the resulting fragments ligated into pGMEGF (digested with Hd3 and Cla1, dephosphorylated with alkaline phosphatase). The ligations were transformed into *E. coli* JS5 (Biorad) by electroporation. Strain JS5 overproduces lac repressor, and is sup0, preventing the expression of the uPA$_{1-48}$-pIII fusion protein due to the amber stop codon between the uPA$_{1-48}$ and the pIII genes. Correct clones were identified by restriction analysis and confined by DNA sequencing. These steps yielded phagemids pHMla (M1Flag-uPA$_{1-48}$) and pHM3a (Glutag-uPA$_{1-48}$). The DNA sequences of the fusion proteins in these phagemids are shown in SEQ ID NO:14 and SEQ ID NO:12.

The phagemid containing a synthetic gene for uPA$_{1-48}$ was constructed in the same vector by the following steps. The sequence of the synthetic gene is shown in SEQ ID NO: 14. Plasmid pCBRuPA (16 µg), a derivative of pCBR (Frederick et al., *J Biol Chem* (1990) 265:3793) containing this synthetic gene for uPA$_{1-48}$, inserted between the yeast α-factor leader and GAPDH terminator as a BglII fragment, was digested with Sac1 and Cla1, and adapted for phagemid expression using the following set of synthetic oligonucleotides:
SRO35: AGCTIAGCGGAATACATGCCAATG-GAAAGCAATGAGCT (SEQ ID NO: 16);
SRO36: CATTGCTTCCATTGGCATGTATTCCGCTAA (SEQ ID NO: 17);
SRO37: CGATAAGTCAAAATAGGGTG (SEQ ID NO:18); and
SRO38: GATCCACCCTATTTTGACTTAT (SEQ ID NO:19).
Oligonucleotides SRo36 and SRo37 (250 pmol) were phosphorylated with polynucleotide kinase and annealed with equimolar amounts of oligos SRo35 and SRo38, respectively. The two annealed duplexes (125 pmol) were ligated overnight with the digested plasmid DNA, the ligase heat inactivated, and the ends phospborylated with polynucleotide kinase. The DNA was run on a 6% polyacrylamide gel and the correct sized band (ca. 200 bp) was excised and isolated. The insert was ligated with plasmid pIHMla (digested with Hd3 and BamHI) and phosphatased, and the ligations transformed into *E. coli* JS5. The correct recombinants were identified by restriction analysis, and confirmed by DNA sequencing, yielding phagemid pHM3–3.
B.) Production and Panning of Phagemids:

To produce phagemid particles, DNAs were transformed into *E. coli* strain XL1-blue (Stratagene) by electroporation. This strain was used because it is supE44 (TAG codon encodes Gln), laciQ (overproduces lac repressor), and makes phage (F'+). Overnight cultures were grown in 2×YT broth containing 50 μg/mL ampicillin and 10 μg/mL tetracycline (to maintain the F'). Cells were diluted 1:50 or 1:100 into the same media, grown for 20 minutes as 37° C. for 10 minutes at 225 rpm to enhance phage attachment, and then grown with normal agitation at 325 rpm overnight. Phage particles were then purified and concentrated by two successive precipitations with polyethylene glycol. The concentrations of phage present were determined by infection of E. coli XL1-blue and plating on L broth plates containing 50 μg/mL ampicillin.

To pan for binding phage particles, small tissue culture plates were coated either with anti-Glu antibody (R. Clark, Onyx Corporation) or streptavidin at 10 μg/mL in PBS overnight. Plates were then blocked with PBS. containing 0.1% BSA. To the streptavidin plates was then added 1 ug/mL of biotinylated secreted human urokinase receptor obtained by recombinant baculovirus infection of A. californica Sf9 cells. After 2 hours at room temperature, the plates were again blocked with BSA, and phage ($10^6$–$10^{10}$ cfu) were added in 1 mL of PBS/BSA. After incubation for 1 hour, non-specifically adhered phage were removed by washing (7×1 mL PBS/BSA), and the remaining phage eluted with 1 mL of 0.1 M glycine, pH 2.2, for 30 minutes. The eluted phage were immediately neutralized with. 1 M Tris, pH 9.4, and stored at 4° C. overnight. The number of phage eluted was determined by titering on E. coli XLI1-blue on ampicillin plates. The procedure, where phage are first bound and eluted from the Glu-Ab plates and then panned against receptor plates, reduces the high background that would otherwise result from the large number of phage containing only wild type pIII: only phage containing an insert in pIII display an epitope tag and are selected on anti-Glu MAbs plates.

Table 2 shows that phagemids displaying $uPA_{1-48}$ are specifically bound and eluted from immobilized urokinase receptor. Table 3 demonstrates that the phagemid which displays a Glu tag-$uPA_{1-48}$ fusion is specifically reied by immobilized Glu Ab. Finally, Table 4 shows that a population of the Glu-$uPA_{1-48}$ phagemid which has been specifically eluted from the Glu Ab plates, is retained with a much higher yield on urokinase receptor plates, than is the unenriched phagemid population.

TABLE 2

Panning on Immobilized Receptor

| | | | % Yield | |
| --- | --- | --- | --- | --- |
| Sample | Phage/phagemid | Input[e] | −uPAR | +uPAR |
| 1[a] | 1a | 9.4 × 10$^9$ | 0.0018 | 0.094 |
| 2[b] | 3a | 1.4 × 10$^{10}$ | 0.0014 | 0.08 |
| 3[c] | pGMEGF | 1.3 × 10$^{10}$ | 0.0015 | 0.0012 |
| 4[d] | LP67 (control) | 1.4 × 10$^9$ | — | 0.0099 |

[a]M1-FLAG-UPAELD-short pIII (pHM1a)
[b]Glu-tag-UPAELD-short pIII (pHM3a)
[c]M1-FLAG-EGF-medium long pIII pGMEGF)
[d]LP67-control phage (Amp$^r$ M 13)
[e]ampicillin resistant colonies, in cfu

TABLE 3

Panning phage with Glu-Ab or suPAR

| | | | % Yield | |
| --- | --- | --- | --- | --- |
| Sample | Phage/phagemid | Input[e] | −uPAR | +uPAR |
| 1 | pHM1a | 1.5 × 10$^{10}$ | 0.55% | 0.003% |
| 2 | pHM3a | 2.5 × 10$^{10}$ | 0.44% | 0.048% |
| 3 | LP67 (control) | 3.5 × 10$^5$ | 0.008% | — |

[a]ampicillin resistant colonies, cfu
[b]soluble uPA receptor

TABLE 4

Panning GluAb-unenriched and enriched phage on suPAR

| | | | % Yield | |
| --- | --- | --- | --- | --- |
| Sample | Phage/phagemid | Input[e] | −uPAR | +uPAR |
| 1 | pHM3a | 2.7 × 10$^7$ | 0.85% | 0.08% |
| 2 | pHM3a (enriched) | 6 × 10$^6$ | 9.7% | 3.3% |
| 3 | LP67 (control) | 5.4 × 10$^6$ | <0.04% | <0.02% |

[a]ampicillin resistant colonies, in cfu
[b]soluble uPA receptor

These enriched phagemid pools are used for multiple mutagenesis strategies in order to identify improved uPA1-48 ligands with altered specificity or improved affinity. For example the region between residues 13 and 32 of human uPA has been implicated in receptor binding (E. Appella et al., J Biol Chem (1987) 262:443740). Key residues in the region from 19–30 can be easily mutated by replacing the region between the unique restriction sites Kpnl and Munl.

In order to rapidly and quantitatively assess the binding affinities of the resulting $uPA_{1-48}$ variants, relatively large quantities of properly folded proteins are required. Although this could be done by bacterial expression, using the phagemid constructs in a sup0 strain and inducing with IPTG, such a strategy yields relatively small amounts of protein in the periplasm. A second strategy is to express the variants in yeast, as described above for the wild type protein. To accomplish this we have constructed a yeast expression vector which enables us to move fragments encoding residues 4–48 of $uPA_{1-48}$ in a single step from the phagemid vectors. This was accomplished as follows: Plasmid pAGaG, identical to pCBR except for a small deletion of an Xba fragment in the ADH2-GAPDH promoter, was digested with Sac1, which cleaves once within the promoter, and then treated with Mung Bean nuclease which destroys the site. Subsequent religation yielded plasmid pAGoG-Sac. Digestion with BglII and treatment with alkaline phosphatase yielded a vector into which was ligated the BglII fragment corresponding to the synthetic gene for $uPA_{1-48}$. Transformation of E. coli strain HB101 to ampicillin resistance and restriction analysis yielded the correct clone. The 2.4 kB BamnH fragment from this plasmid (pAGaG-Sacl-48synth), containing the expression cassette, was isolated and ligated into pAB24, which had been treated with Bamli and alkaline phosphatase. The resulting plasmid has unique Sacl and Xhol sites which can be used for transfer of the phagemid 1–48 genes. This is accomplished by digesting the phagemid with BamHI, treating with Mung Bean Nuclease, digesting with Sacl and isolating the 145 bp fragment. The vector is digested with Xhol, treated with Mung Bean Nuclease, digested with Sacl, and treated with alkaline phosphatase. Ligation then yields the correct recombinants in a single step in the yeast expression vector. Transformation of yeast strain AB110 then yields high levels of secreted 1–48 variants for analysis.

Using this construct, one can express a library of uPA variations for screening. Variations may be constructed by a variety of methods, including low-fidelity PCR (which introduces a large number of random point mutations), site-specific mutation, primer-based mutagenesis, and ligation of the uPA$_{1-48}$ sequence (or portions thereof) to a random oligonucleotide sequence (e.g., by attaching (NNS). to the uPA$_{1-48}$ coding sequence, or substituting NNS for one or more uPA$_{1-48}$ codons). Generation of random oligonucleotide sequences is detailed in Devlin, WO91/18980, incorporated herein by reference. Phage displaying uPA$_{1-48}$ variants (having one or more amino acid substitutions) are screened according to the protocol described above (using, e.g., pHM3a as a positive control) and selected for improved binding.

Example 5

(Formulation of huPA$_{1-48}$)

huPA$_{1-48}$ formulations suitable for use in chemotherapy are prepared as follows:

| A) | Injectable Formulation: | | |
|---|---|---|---|
| | huPA$_{1-48}$ | | 7.0 mg |
| | Na$_2$HPO$_4$ (0.5M) | | 0.5 mL |
| | mannitol (25%) | | 2.5 mL |
| | sodium laureate (1%) | | 2.5 mL |
| | pH | | 7.5 |
| | PBS qs | | 20 mL |

This formulation is prepared following the procedure set forth in U.S. Pat. No. 4,816,440, incorporated herein by reference. The formulation is administered by parenteral injection at the site to be treated. The formulation is also generally suitable for administration as eyedrops directly to the conjunctiva, or by intranasal administration as an aerosol. Alternatively, a concentrated formulation (e.g., reducing the phosphate buffered saline to 2 mL) may be used to fill an Alzet® minipump, and the minipump implanted at the site to be treated.

| B) | Ophthalmic Preparation: | | |
|---|---|---|---|
| | huPA$_{1-48}$ | | 1 mg |
| | fibronectin | | 69 mg |
| | albumin | | 37.5 mg |
| | water | qs | 3.0 mL |
| | HCl (0.01M) | qs | pH 4.0 |

This dosage form is prepared following the procedure set forth in U.S. Pat. No. 5,124,155, incorporated herein by reference. The fibronectin and albumin are dissolved in water to form a 3.0 mL solution, and HCl added to a pH of 4.0, causing the fibronectin to flocculate. The flocculent is filtered, and combined with the huPA$_{1-48}$. The mixture is then placed in a contact lens mold, and the mold closed for 30 min to form a corneal "shield" in the shape of a contact lens. The shield releases huPA$_{1-48}$ over a period of time, and is useful for preventing angiogenesis of corneal tissue following ophthalmic surgery.

The present invention has been described with reference to specific embodiments. However, this application is intended to cover those changes and substitutions which may be made by those skilled in the art without departing from the spirit and the scope of the appended claims.

What is claimed:

1. An unfucosylated huPAR antagonist polypeptide, which polypeptide comprises at most the 48 amino-terminal amino acid residues of huPA (huPA$_{1-48}$), wherein huPA$_{1-48}$ has the polypeptide sequence Ser-Asn-Glu-Leu-His-Gln-Val-Pro-Ser-Asn-Cys-Asp-Cys-Leu-Asn-Gly-Gly-Thr-Cys-Val-Ser-Asn-Lys-Ty-Phe-Ser-Asn-Be-His-Tm-Cys-Asn-Cys-Pro-Lys-Lys-Phe-Glv-Gly-Gln-His-Cys-Glu-Ile-Asp-Lys-Ser-Lys (SEQ ID NO:22), or comprises an active analog thereof, wherein an active analog refers to a polypeptide that differs from said huPA$_{1-48}$ (SEQ ID NO:22) by at most one to seven amino acids, and having a binding affinity that is substantially the same or greater than that of huPA$_{1-48}$ (SEQ ID NO:22) with huPAR.

2. The unfucosylated huPAR antagonist polypeptide of claim 1 which is huPA$_{1-48}$ SEQ ID NO: 22.

3. The unfucosylated huPAR antagonist polypeptide according to claim 1 which comprises from one to seven conservative amino acid substitutions relative to huPA$_{1-48}$ SEQ ID NO: 22.

4. The unfucosylated huPAR antagonist polypeptide according to claim 1, which comprises a deletion of one to seven amino acids relative to huPA$_{1-48}$ SEQ ID NO: 22.

5. The unfucosylated huPAR antagonist polypeptide according to claim 1, which comprises at least one conservative amino acid substitution.

6. The unfucosylated huPAR antagonist polypeptide according to claim 1, which possesses a K$_d$ of about 0.3 nM.

7. A composition comprising an unfucosylated huPAR antagonist according to claim 1 and a carrier.

8. A composition comprising an unfucosylated huPAR antagonist according to claim 2 and a carrier.

9. A composition comprising an unfucosylated huPAR antagonist according to claim 3 and a carrier.

10. A composition comprising an unfucosylated huPAR antagonist according to claim 4 and a carrier.

11. A composition comprising an unfucosylated huPAR antagonist according to claim 5 and a carrier.

12. A composition comprising an unfucosylated huPAR antagonist according to claim 6 and a carrier.

13. A composition according to claim 7 wherein said carrier comprises a pharmaceutically acceptable excipient.

14. A composition according to claim 8 wherein said carrier comprises a pharmaceutically acceptable excipient.

15. A composition according to claim 9 wherein said carrier comprises a pharmaceutically acceptable excipient.

16. A composition according to claim 10 wherein said carrier comprises a pharmaceutically acceptable excipient.

17. A composition according to claim 11 wherein said carrier comprises a pharmaceutically acceptable excipient.

18. A composition according to claim 12 wherein said carrier comprises a pharmaceutically acceptable excipient.

* * * * *